ize Patent [19]

Hatano et al.

[11] Patent Number: 4,711,867
[45] Date of Patent: Dec. 8, 1987

[54] CATALYTIC COMPOSITION

[75] Inventors: Masakatsu Hatano, Yokohama; Kazunori Oshima, Tokyo; Tatsuya Ihara, Kurashiki; Kenichi Kiyono, Hachioji, all of Japan

[73] Assignee: Mitsubishi Chemical Industries Limited, Tokyo, Japan

[21] Appl. No.: 833,279

[22] Filed: Feb. 27, 1986

[30] Foreign Application Priority Data

Mar. 7, 1985 [JP] Japan .................................. 60-45186

[51] Int. Cl.$^4$ ............................................. B01J 21/02
[52] U.S. Cl. .................................... 502/205; 502/201; 502/204; 502/206; 558/324
[58] Field of Search ................. 502/201, 204, 205, 206

[56] References Cited

U.S. PATENT DOCUMENTS

| | | | |
|---|---|---|---|
| 3,226,422 | 12/1965 | Sennewald et al. | 502/212 X |
| 3,542,843 | 11/1970 | Yoshino et al. | 502/206 X |
| 4,036,901 | 7/1977 | Kawakami et al. | 585/431 |
| 4,065,468 | 12/1977 | Grosselli et al. | 502/206 X |
| 4,083,804 | 4/1978 | Saito et al. | 502/204 X |
| 4,093,558 | 6/1978 | Grosselli et al. | 502/206 |
| 4,167,494 | 9/1979 | Grosselli et al. | 502/206 X |
| 4,207,212 | 6/1980 | Nefedor et al. | 502/252 |
| 4,283,307 | 8/1981 | Barone et al. | 502/205 |
| 4,456,563 | 6/1984 | Katsumoto et al. | 558/308 |

FOREIGN PATENT DOCUMENTS

| | | | |
|---|---|---|---|
| 0015565 | 9/1980 | European Pat. Off. | 502/205 |
| 45-32685 | 10/1970 | Japan | 502/205 |
| 57-123122 | 7/1982 | Japan | 502/205 |

Primary Examiner—Andrew Metz
Assistant Examiner—William G. Wright
Attorney, Agent, or Firm—Oblon, Fisher, Spivak, McClelland, & Maier

[57] ABSTRACT

A catalystic composition suitable for producing acrylonitrile from propylene, ammonia and oxygen (or oxygen-containing gas), which composition is represented by the following formula:

$$(Mo)_a(W)_b(Bi)_c(Pb)_d(B)_e(Sb)_f(X)_g(O)_h$$

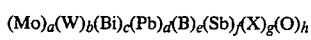

(where: X is chromium or iron; a, b, c, d, e, f, g and h denote respectively number of atoms for molybdenum, tungsten, bismuth, lead, boron, antimony, X and oxygen, and wherein, if it is given that $a+b=12$, $0 \leq b \leq 7$, $0.4 \leq c \leq 7$, $2 \leq d \leq 12$, $0.2/22 \leq e/a \leq 40/22$, $0 \leq f/a \leq 25/22$, and $0 \leq g/a \leq 3/22$; and h denotes the number of oxygen necessary for satisfying the atomic valence for the individual constituent elements other than oxygen).

3 Claims, No Drawings

CATALYTIC COMPOSITION

The present invention relates to a catalytic composition, and, more particularly, it is concerned with a catalytic composition which exhibits a marked catalytic effect in the reaction to produce acrylonitriles by the vapor-phase reaction of propylene, ammonia, and oxygen (or an oxygen-containing gas).

Various catalysts have heretofore been proposed as the catalysts for the so-called "ammoxidation" for the production of acrylonitrile by contacting propylene, ammonia, and oxygen (or oxygen-containing gas) in the vapor-phase. For instance, Japanese Patent Publication No. 22138/1963 discloses a method for preparing P-Mo-Bi-B-O type catalyst, and Japanese Unexamined Patent Publication No. 143843/1983 discloses a method for preparing multi-component oxide catalysts containing therein Mo, Bi and B.

However, these catalysts are not yet satisfactory in suppressing side reactions, and, when the rate of conversion of propylene is increased, the selectivity of the catalyst is so decreased that it becomes difficult to achieve a satisfactorily high yield of acrylonitrile.

On the other hand, it has been known that an Mo-Bi-W-Pb-O type catalyst has high catalytic effect in the production of acrylonitrile (vide: Japanese Patent Publication No. 32618/1982).

The present inventors conducted studies and researches in an attempt to develop a catalyst capable of producing acrylonitrile at high selectivity, when boron is added to the Mo-Bi-Pb-O or Mo-Bi-W-Pb-O type catalyst. As the result of such research activities, they found that, when use is made of a catalyst containing molybdenum, bismuth, lead, boron and oxygen in a particular compositional range, or a catalyst obtained by adding specific quantities of tungsten, antimony, chromium and/or iron to the above-mentioned catalytic elements, it was possible to obtain acrylonitrile with much improved rate of yield, and that such high yield could be sustained over a long period of time. On the basis of this finding, they arrived at the present invention.

It is therefore an object of the present invention to provide a catalytic composition which can be used advantageously for commercial production of acrylonitrile.

In accordance with the present invention, the above-mentioned objective is accomplished by a catalytic composition having the following formula:

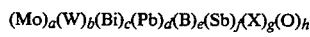
$(Mo)_a(W)_b(Bi)_c(Pb)_d(B)_e(Sb)_f(X)_g(O)_h$ (where: X is chromium or iron; a, b, c, d, e, f, g and h respectively denote number of atoms for molybdenum, tungsten, bismuth, lead, boron, antimony, X and oxygen, wherein, if it is given that $a+b=12$, $0 \leq b \leq 7$, $0.4 \leq c \leq 7$, $2 \leq d \leq 12$, $0.2/22 \leq e/a \leq 40/22$, $0 \leq f/a \leq 25/22$, $0 \leq g/a \leq 3/22$; and h denotes the number of oxygen necessary for satisfying the atomic valence for the individual constituent elements other than oxygen).

In order to improve the rate of yield of acrylonitrile, particularly suitable number of atoms for each of the individual constituent elements in the catalytic composition according to the present invention are as follows: if it is given that $a+b=12$, $0 \leq b \leq 5.5$, $0.6 \leq c \leq 6$, $3 \leq d \leq 11$, $0.3/22 \leq e/a \leq 30/22$, $0.5/22 \leq f/a \leq 18/22$, $0.05/22 \leq g/a \leq 2/22$.

The chemical structure of the catalytic composition according to the present invention, though it cannot be defined precisely, should preferably contain lead molybdate as the principal constituent, in which bismuth and boron are present in solid-solution, as the result of observation by the X-ray diffraction.

The catalytic composition of the present invention may be shaped, as it is, without use of a carrier. It may also be shaped by use of the carrier such as silica, alumina, titania, silicon carbide, and so forth. The size and geometry of the shaped catalyst are not particularly limitative, and the catalytic composition may be shaped into catalyst particles of any arbitrary shape and size (such as, for example, pellets, tablets, spherulites, granules, and others) depending on the conditions, under which it is used.

Molybdenum compounds useful for the preparation of the catalytic composition of this invention include molybdenum oxides such as molybdenum trioxide, etc., molybdic acid or its salts; and phosphomolybdic acid or its salts. Among these molybdenum compounds, molybdates such as ammonium paramolybdate are used preferably.

Useful tungsten compounds include tungsten oxides such as tungsten trioxide, etc., tungstic acid, or its condensed acids, or their salts; and phosphotungstic acid or its salts.

Bismuth compounds that can be used of the purpose of this invention include bismuth salts such as bismuth nitrate, bismuth sulfate, etc.; and various oxides and hydroxides of bismuth.

As lead compounds useful for the purpose of this invention, there may be exemplified lead salts such as lead nitrate, lead sulfate, and so on; and various oxides and hydroxides of lead.

As boron compounds, there may be used boric acid; borates such as ammonium borate; and boric acid esters such as trimethyl borate, etc.; and boron oxide.

Useful antimony compounds include oxides such as antimony trioxide; chlorides such as antimony trichloride; and metallic antimony.

Useful chromium compounds include chromium salts such as chromium nitrate, chromium sulfate, ammonium dichromate, etc.; and various oxides and hydroxides of chromium.

Useful iron compounds include iron salts such as iron nitrate and iron sulfate; and various oxides and hydroxides of iron.

For preparation of the catalytic composition using these starting materials, the compounds of the constituent elements are dissolved or suspended in water, and, in some cases, a sol of a carrier material such as silica sol and alumina sol, or carrier particles such as titania powder are suspended in water to render the material into a uniform slurry or aqueous solution, followed by calcining the same.

In case the catalytic composition is shaped by spray drying, the pH value of the material slurry is controlled between 1 and 6 before drying, there can be obtained the catalytic composition excellent in its shock-resistant property.

In the production of the catalytic composition, when aqueous solution of ammonium paramolybdate and ammonium paratungstate are used as the molybdenum compound and the tungsten compound, respectively, it is preferable to add a solubility stabilizer such as ammonia to the aqueous solution containing therein salts of these compounds, for increasing the stability in its dissolution.

In the case where bismuth nitrate or bismuth sulfate is employed as the bismuth compound, it is preferable that the compounds be rendered aqueous solution of nitric acid and aqueous solution of sulfuric acid, respectively. When antimony trioxide is used as the antimony compound, it may be used by dissolving in an aqueous solution of an organic acid such as tartaric acid, etc. However, in the case of using antimony trioxide powder, the resulting final slurry containing all the catalytic components may preferably be uniformly stirred, adjusted to a pH value of 7 or less, and heat-treated for a period of from 1 to 8 hours at a temperature of 40° C. or higher.

Following the shaping step, the shaped catalyst particles are usually calcined for 5 minutes to four hours at a temperature in the range of from 400° C. to 800° C., or preferably from 500° C. to 750° C., although the temperature and duration of the calcination step are not particularly limited to these alone.

In order to produce acrylonitrile, propylene, ammonia and oxygen (or an oxygen-containing gas) are brought into contact in the vapor-phase in the presence of the catalytic composition according to the present invention. It is not always necessary that propylene gas as the starting material is of high purity. It may contain therein a substantial amount of other gas which is substantially inert to the reaction such as, for example, saturated hydrocarbon like propane, etc. In the commercial production, air is usually employed as the oxygen-containing gas. The molar ratio of oxygen to propylene is usually in a range of 1:1 to 4:1, or preferably 1.5:1 to 2.5:1. The molar ratio of ammonia to propylene fed to the reaction zone is usually in a range of 0.8:1 to 2.5:1, or preferably 0.9:1 to 1.5:1. The reaction is usually conducted under the atmospheric pressure, but it may be carried out at a sub-atmospheric or super-atmospheric pressure, as the case may be. The reaction temperature usually ranges from 360° C. to 540° C., or preferably from 400° C. to 500° C. The space velocity, at which the starting gaseous reactants are fed, may be suitably selected from the range of 100 to 3,000 hr$^{-1}$, or preferably from 200 to 2,000 hr$^{-1}$.

The catalytic composition of this invention may be used either in the fixed bed or fluidized bed system.

As has been explained in detail in the foregoing, the catalytic composition according to the present invention is capable of forming acrylonitrile with high selectivity even at an increased conversion of the starting gaseous material by the ammoxidation of propylene, hence it can be employed in the commercial production of acrylonitrile with advantage.

Having generally described the present invention, a more complete understanding thereof can be obtained by reference to certain preferred examples which are provided herein for the purposes of illustration alone, and are not intended to limit the scope of the invention in any manner.

The terms "conversion", "selectivity", and "yield of acrylonitrile" as used herein are defined by the following equations.

$$\text{Conversion (\%)} = \frac{\text{Moles of propylene consumed}}{\text{Moles of propylene fed}} \times 100$$

$$\text{Selectivity (\%)} = \frac{\text{Moles of acrylonitrile formed}}{\text{Moles of propylene consumed}} \times 100$$

Yield of acrylonitrile (%) = [Conversion (%)] × [Selectivity (%)] × 1/100

EXAMPLE 1

To 1.5 ml of 1 wt. % aqueous ammonia solution containing therein 0.1 mol/l of ammonium paratungstate [(NH$_4$)$_{10}$W$_{12}$O$_{41}$.5H$_2$O] as the tungsten source, 15.03 g of 20 wt. % silica sol was added. Subsequently, the following solutions were added under agitation: (a) 9.15 ml of aqueous solution containing therein 1 mol/l of lead nitrate [Pb(NO$_3$)$_2$] as the lead source; (b) 12.6 ml of 5 wt. % aqueous ammonia solution containing therein 1 mol/l of ammonium paramolybdate [(NH$_4$)$_6$Mo$_7$O$_{24}$ 4H$_2$O] as the molybdenum source; and (c) 2.4 ml of 10 wt. % aqueous solution of nitric acid containing therein 1 mol/l of bismuth nitrate as the bismuth source. Then, 3.44 ml of aqueous solution containing therein 0.5 mol/l of boric acid (H$_3$BO$_3$) as the boron source was added to the above-mentioned mixture solution with further addition of 10 wt. % aqueous solution of nitric acid to adjust the pH value of the mixture solution to 2.2, and then the resulted slurry was heated under agitation on a hot plate until the evolution of NO$_2$ ceased. The heating was continued until the slurry was evaporated to dryness. The thus obtained solid residue was shaped under compressive force into tablets of 6 mm in diameter and 3 mm in thickness, which were calcined at 600° C. for 2 hours in a stream of air. Thereafter, the solid product was crushed to give a catalyst in the form of granules of 16 to 24 meshes in size (in accordance with the Tyler standard).

The thus obtained catalyst had the following composition: Mo$_{11.8}$W$_{0.14}$Bi$_{2.26}$Pb$_{8.63}$B$_{1.62}$O$_{50.45}$. The weight ratio of silica as the carrier to the total catalytic components was 40:60. 1 ml of the catalyst was charged into a heat-resistant glass reactor, and then, a mixed gas of propylene, ammonia and air at a molar ratio of propylene to ammonia to air of 1:1.2:10 was fed into the tubular reactor at a space velocity of 500 hr$^{-1}$, and then the reaction was carried out at a temperature of 460° C. The results are shown in Table 1 below.

EXAMPLES 2 to 6

In the same manner as in Example 1 above, various catalysts of the composition as indicated in Table 1 were prepared and used for the same reaction as conducted in Example 1 above. The results are also shown in Table 1 below.

EXAMPLE 7

To 1.5 ml of 1 wt. % aqueous ammonia solution containing therein 0.1 mol/l of ammonium paratungstate [$(NH_4)_{10}W_{12}O_{41}.5H_2O$] as the tungsten source, there was added 15.51 g of 20 wt. % silica sol. Subsequently, the following solutions were added under agitation: (a) 9.15 ml of aqueous solution containing therein 1 mol/l of lead nitrate [$Pb(NO_3)_2$] as the lead source; (b) 12.6 ml of 5 wt. % of aqueous ammonia solution containing therein ammonium paramolybdate [$(NH_4)_6Mo_7O_{24}.4H_2O$] as the molybdenum source; and (c) 2.4 ml of 10 wt. % aqueous solution of nitric acid containing therein 1 mol/l of bismuth nitrate [$Bi(NO_3)_3.5H_2O$] as the bismuth source. Then 29.15 g of antimony trioxide ($Sb_2O_3$) in powder form and available in general market was mixed with 120 ml of water, 21.2 ml of 25 wt. % ammonia water, and 45.04 g of tartaric acid, followed by dissolving the mixture under heat. Thereafter, the slurry was diluted with water, to which 2.86 ml of solution parepared to contain therein 0.2 mol/l of antimony and 6.87 ml of aqueous boric acid ($H_3BO_3$) solution containing therein 0.5 mol/l of boron source were further added. Furthermore, 10 wt. % aqueous solution of nitric acid was added to above-mentioned slurry to adjust the pH value thereof to 2.2.

The thus obtained slurry was treated in the same manner as in Example 1 above to prepare the catalytic composition, and then the same reaction as conducted in Example 1 above was done. The catalytic composition as well as the reaction results are shown in Table 1 below.

EXAMPLES 8 to 14

In the same manner as in Example 7 above, the catalyst of the composition as shown in Table 1 below was prepared, and the same reaction as in Example 1 above was conducted. The catalyst composition as well as the reaction results are shown in Table 1 below. As is apparent from Examples 7 to 14, the inclusion of antimony as the catalytic component further improves the reaction results.

EXAMPLES 15 to 17

The same process operations as in Example 7 above were followed with the exception that the pH value before the slurry was evaporated to dryness was changed from 2.2 to 4.0 to thereby prepare the catalysts of the compositions as indicated in Table 1 below. Then, the same reaction as in Example 1 above was carried out. The catalyst compositions as well as the reaction results are shown in Table 1 below.

COMPARATIVE EXAMPLE 1

The same experiment as in Example 1 above was repeated with the exception that the adding quantity of boron in Example 1 was increased. The catalyst composition and the reaction results are as shown in Table 2 below.

COMPARATIVE EXAMPLE 2

The same experiment as in Example 1 above was repeated with the exception that the addition of boron in Example 1 was omitted. The catalyst composition and the reaction results are as shown in Table 2 below.

COMPARATIVE EXAMPLE 3

To 12.79 g of 20 wt. % silica sol, the following solutions were added under agitation: (a) 12 ml of 5 wt. % aqueous ammonia solution containing therein 1 mol/l of ammonium paramolybdate [$(NH_4)_6Mo_7O_{24}.4H_2O$] as the molybdenum source; (b) 8 ml of 10 wt. % aqueous nitric acid solution containing therein 1 mol/l of bismuth nitrate [$Bi(NO_3)_3.5H_2O$] as the bismuth source; and (c) 14.18 ml of aqueous boric acid solution containing therein 0.5 mol/l of boric acid ($H_3BO_3$) as the boron source. Thereafter, 10 wt. % of aqueous nitric acid solution was added to the slurry to adjust its pH value to 2.2.

The resulted slurry was treated in the same manner as in Example 1 above and made into the catalyst composition, which was used for the same reaction as in Example 1 above. The catalyst composition and the reaction results are as shown in Table 2 below.

COMPARATIVE EXAMPLE 4

The same experiment as in Example 1 above was repeated with the exception that the adding quantity of boron in Example 1 was decreased. The catalyst composition and the reaction results are as shown in Table 2 below.

EXAMPLE 18

To 1.5 ml of 1 wt. % of aqueous ammonia solution containing therein 0.1 mol/l of ammonium paratungstate [$(NH_4)_{10}W_{12}O_{41}.5H_2O$] as the tungsten source, 15.89 g of 20 wt. % silica sol was added. Subsequently, the following solutions were added under agitation: (a) 9.15 ml of aqueous solution containing therein 1 mol/l of lead nitrate [$Pb(NO_3)_2$] as the lead source; (b) 12.6 ml of 5 wt. % aqueous ammonia solution containing therein 1 mol/l of ammonium paramolybdate [$(NH_4)_6Mo_7O_{24}.4H_2O$] as the molybdenum source; and (c) 2.4 ml of 10 wt. % aqueous nitric acid solution containing therein 1 mol/l of bismuth nitrate [$Bi(NO_3)_3.5H_2O$] as the bismuth source. Then, 29.15g of antimony trioxide ($Sb_2O_3$) in powder form and available in general market was mixed with 120 ml of water, 21.2 ml of 25 wt. % ammonia water, and 45.04 g of tartaric acid, and the thus obtained mixture was dissolved under heat. Thereafter, the slurry was diluted with water in a mesflask, to which 7.14 ml of solution prepared to contain therein 0.2 mol/l of antimony was added to the abovementioned slurry, and, therafter, the following solutions were added to the slurry: (a) 1.14 ml of aqueous solution containing therein 0.1 mol/l of chromium nitrate [$Cr(NO_3)_3.9H_2O$] as the chromium source; and (b) 5.71 ml of aqueous solution containing therein 0.5 mol/l of boric acid ($H_3BO_3$) as the boron source with further addition of 10 wt. % aqueous nitric acid solution to adjust the pH value of the mixture solution to 2.2, and then the resulted slurry was heated under agitation on a hot plate until the evolution of $NO_2$ ceased. The heating was continued until the slurry was evaporated to dryness. The thus obtained solid residue was shaped under compressive force into tablets of 6 mm in diameter and 3 mm in thickness, which were calcined at 630° C. for 2 hours in a stream of air. Thereafter, the solid product was crushed to give a catalyst in the form of granules of 16 to 24 meshes in size (in accordance with the Tyler standard).

The thus obtained catalyst had the following composition:

$Mo_{11.86}W_{0.14}Bi_{2.26}Pb_{8.63}Cr_{0.11}Sb_{1.35}B_{2.70}O_{54.26}$. The weight ratio of silica as the carrier to the total catalytic components was 40:60. 1 ml of this catalyst was charged into a heat-resistant glass reactor, and then, a mixed gas of propylene, ammonia and air at a molar ratio of propylene to ammonia to air of 1:1.2:10 was fed into the tubular reactor at a space velocity of 500 hr$^{-1}$, and then the reaction was carried out at a temperature of 460° C. The results of the reaction after lapse of 2 hours are as shown in Table 3 below.

EXAMPLES 19 to 26

In the same manner as in Example 18 above, the catalysts of the compositions as shown in Table 1 below were prepared, and they were used for the reaction in the same manner as in Example 18. The results of the reaction after lapse of 2 hours are also shown in Table 3 below.

EXAMPLES 27 and 28

The same experiment as in Example 1 above was repeated with the exception that aqueous solution of ferric nitrate [Fe(NO$_3$)$_3$.9H$_2$O] at a rate of 0.1 mol/l as the iron source was used in place of chromium nitrate as used in Example 18 above, and that calcination was carried out at 680° C. The catalyst compositions and the reaction results after lapse of 2 hours are as shown in Table 4 below.

EXAMPLES 29 and 30

The catalysts of the same compositions as in Examples 18 and 27 were used for the reaction over a long period of time under the same reaction conditions as in Example 18 above. The results of the reaction after lapse of 100 hours are shown in Table 4 below. From comparison of Example 27 and Comparative Example 5, it is seen that the catalyst of the present invention is able to maintain its catalytic effect over a long period of time.

COMPARATIVE EXAMPLE 5

The catalyst of the composition as indicated in Table 5 below was prepared in the same manner as in Example 18 above with the exception that the addition of chromium nitrate was omitted. Then, the resulted catalyst was used for the reaction over a long period of time under the same conditions as in Example 18. The results of the reaction after lapse of 100 hours are shown in Table 4 below. From comparison of Example 27 and Comparative Example 5, it is seen that the catalyst according to the present invention is able to maintain its catalytic effect over a long period of time.

COMPARATIVE EXAMPLE 6

The same experiment as in Example 18 above was repeated with the exception that the addition of boron in Example 18 was omitted. The catalyst composition and the reaction results after lapse of 2 hours are shown in Table 5 below.

COMPARATIVE EXAMPLE 7

The same experiment as in Example 18 above was repeated with the exception that the adding quantity of chromium nitrate in Example 18 was increased. The catalyst composition and the reaction results after lapse of 2 hours are shown in Table 5 below.

EXAMPLE 31

The same experiment as in Example 18 above was repeated with the exception that the addition of ammonium paratungstate was omitted. The resulted catalyst had the following composition: $Mo_{12.0}Bi_{2.29}Pb_{8.71}B_{2.72}Sb_{1.36}Cr_{0.11}O_{54.43}$. After 2 hour's reaction, the conversion was 97.8%, the selectivity toward acrylonitrile was 88.1%, and the yield of acrylonitrile was 86.2%.

TABLE 1

| Example No. | Composition of catalyst (atomic ratio) | | | | | | | Reaction temperature (°C.) | Conversion of propylene (%) | Selectivity toward acrylonitrile (%) | Yield of acrylonitrile (%) |
|---|---|---|---|---|---|---|---|---|---|---|---|
| | Mo | W | Bi | Pb | B | Sb | O | | | | |
| 1 | 11.86 | 0.14 | 2.26 | 8.61 | 1.62 | | 50.43 | 460 | 100 | 72.0 | 72.0 |
| 2 | " | " | " | " | 3.23 | | 52.85 | " | " | 73.3 | 73.3 |
| 3 | " | " | " | " | 5.39 | | 56.09 | " | " | 76.3 | 76.3 |
| 4 | " | " | " | " | 7.01 | | 58.52 | " | " | 77.9 | 77.9 |
| 5 | " | " | " | " | 10.78 | | 64.17 | " | 99.8 | 80.2 | 80.0 |
| 6 | " | " | " | " | 14.02 | | 69.03 | " | 98.2 | 82.6 | 81.1 |
| 7 | " | " | " | " | 1.62 | 0.54 | 51.24 | " | 100 | 81.0 | 81.0 |
| 8 | " | " | " | " | 3.23 | " | 53.66 | " | 99.8 | 85.2 | 85.0 |
| 9 | " | " | " | " | 4.85 | " | 56.09 | " | 99.0 | 87.1 | 86.2 |
| 10 | " | " | " | " | 6.47 | " | 58.52 | " | 98.1 | 88.4 | 86.4 |
| 11 | " | " | " | " | 8.63 | " | 61.76 | 470 | 98.0 | 88.0 | 86.2 |
| 12 | " | " | " | " | 10.78 | " | 64.98 | 480 | 96.7 | 88.0 | 85.1 |
| 13 | " | " | " | " | 3.23 | 1.08 | 54.47 | 470 | 96.6 | 89.0 | 86.0 |
| 14 | " | " | " | " | 0.27 | 2.16 | 51.65 | 460 | 98.8 | 87.2. | 86.2 |
| 15 | " | " | " | " | 2.70 | 2.70 | 56.1 | " | 98.0 | 88.6 | 86.9 |
| 16 | " | " | " | " | " | 3.77 | 57.7 | 470 | 96.9 | 89.1 | 86.4 |
| 17 | " | " | " | " | 0.27 | 4.85 | 55.68 | 460 | 97.9 | 87.7 | 85.8 |

TABLE 2

| Example No. | Composition of catalyst (atomic ratio) | | | | | | Reaction temperature (°C.) | Conversion of propylene (%) | Selectivity toward acrylonitrile (%) | Yield of acrylonitrile (%) |
|---|---|---|---|---|---|---|---|---|---|---|
| | Mo | W | Bi | Pb | B | O | | | | |
| 1 | 11.86 | 0.14 | 2.26 | 8.61 | 28.03 | 90.05 | 490 | 63.2 | 67.7 | 42.8 |
| 2 | " | " | " | " | | 48.0 | 460 | 100.0 | 70.4 | 70.4 |
| 3 | 12.0 | 0 | 8 | 0 | 7.09 | 58.64 | " | 98.1 | 70.3 | 69.0 |
| 4 | 11.86 | 0.14 | 2.26 | 8.61 | 0.05 | 48.08 | " | 100.0 | 70.6 | 70.6 |

TABLE 3

| Example No. | Composition of catalyst (atomic ratio) | | | | | | | | Reaction temperature (°C.) | Conversion of propylene (%) | Selectivity toward acrylonitrile (%) | Yield of acrylonitrile (%) |
|---|---|---|---|---|---|---|---|---|---|---|---|---|
| | Mo | W | Bi | Pb | B | Sb | Cr | O | | | | |
| 18 | 11.86 | 0.14 | 2.26 | 8.61 | 2.69 | 1.35 | 0.11 | 54.23 | 460 | 98.0 | 88.5 | 86.7 |
| 19 | 10.71 | 1.29 | 3.42 | 6.85 | 4.07 | 1.14 | 0.16 | 56.04 | " | " | 86.9 | 85.2 |
| 20 | 11.89 | 0.11 | 3.39 | 6.91 | 4.04 | 1.05 | " | 55.87 | " | 97.4 | 88.4 | 86.2 |
| 21 | 11.85 | 0.15 | 1.74 | 9.39 | 2.07 | 1.20 | 0.08 | 53.03 | " | 98.7 | 87.8 | 86.7 |
| 22 | 7.07 | 4.93 | 0.99 | 10.52 | 1.18 | 0.87 | 0.05 | 51.16 | " | 98.1 | 88.0 | 86.3 |
| 23 | 11.28 | 0.72 | 2.40 | 8.40 | 2.86 | 1.31 | 0.11 | 54.42 | " | 97.5 | 88.6 | 86.4 |
| 24 | 11.36 | 0.64 | 3.43 | 6.86 | 4.08 | 0.98 | 0.16 | 55.84 | " | 99.2 | 86.5 | 85.8 |
| 25 | 11.86 | 0.14 | 2.26 | 8.61 | 2.69 | 2.00 | 0.61 | 55.95 | " | 98.4 | 87.4 | 86.0 |
| 26 | " | " | " | " | 8.07 | 0.81 | 0.11 | 61.49 | " | " | 87.7 | 86.3 |

TABLE 4

| Example No. | Composition of catalyst (atomic ratio) | | | | | | | | | Reaction temperature (°C.) | Reaction time (hr) | Conversion of propylene (%) | Selectivity toward acrylonitrile (%) | Yield of acrylonitrile (%) |
|---|---|---|---|---|---|---|---|---|---|---|---|---|---|---|
| | Mo | W | Bi | Pb | B | Sb | Cr | Fe | O | | | | | |
| 27 | 11.86 | 0.14 | 2.26 | 8.61 | 5.38 | 0.97 | | 0.28 | 57.95 | 460 | 2 | 97.5 | 88.0 | 85.8 |
| 28 | " | " | " | " | 2.69 | 1.57 | | 0.61 | 55.31 | " | " | 98.2 | 87.2 | 85.6 |
| 29 | " | " | " | " | " | 1.35 | 0.11 | | 54.23 | " | 100 | 99.1 | 87.4 | 86.6 |
| 30 | " | " | " | " | 5.38 | 0.97 | | 0.28 | 57.95 | " | " | 98.8 | 86.8 | 85.2 |

TABLE 5

| Comparative Example No. | Composition of catalyst (atomic ratio) | | | | | | | | Reaction temperature (°C.) | Reaction time (hr) | Conversion of propylene (%) | Selectivity toward acrylonitrile (%) | Yield of acrylonitrile (%) |
|---|---|---|---|---|---|---|---|---|---|---|---|---|---|
| | Mo | W | Bi | Pb | B | Sb | Cr | O | | | | | |
| 5 | 11.86 | 0.14 | 2.26 | 8.61 | 6.47 | 0.54 | | 58.52 | 460 | 2 | 98.1 | 88.4 | 86.4 |
| | " | " | " | " | " | " | | " | " | 100 | 95.2 | 84.0 | 80.0 |
| 6 | " | " | " | " | | 1.35 | 0.11 | 50.19 | " | 2 | 100 | 82.2 | 82.2 |
| 7 | " | " | " | " | 2.69 | " | 2.70 | 58.11 | " | " | " | 77.5 | 77.5 |

We claim:

1. A catalyst composition for the production of acrylonitrile from propylene, ammonia and oxygen or an oxygen-containing gas of the formula:

$$(Mo)_a(W)_b(Bi)_c(Pb)_d(B)_e(Sb)_f(X)_g(O)_h$$

wherein X is chromium or iron; a, b, c, d, e, f, g and h respectively denote the number of atoms of molybdenum, tungsten, bismuth, lead, boron, antimony, element X and oxygen, wherein, given that $a+b=12$, $0 \leq b \leq 7$, $0.4 \leq c \leq 7$, $2 \leq d \leq 12$, $0.2/22 \leq e/a \leq 40/22$, $0 \leq f/a \leq 25/22$, $0 \leq g/a \leq 3/22$; and h denotes the number of oxygen atoms necessary to satisfy the valencies of the remaining constituent elements of the catalyst.

2. The catalyst composition of claim 1, wherein said catalyst is supported on a carrier selected from the group consisting of silica, alumina, titania and silicon carbide.

3. The catalyst composition of claim 1, wherein, given that $a+b=12$, $0 \leq b \leq 5.5$, $0.6 \leq c \leq 6$, $3 \leq d \leq 11$, $0.3/22 \leq e/a \leq 30/22$, $0.5/22 \leq f/a \leq 18/22$ $0.05/22 \leq g/a \leq 2/22.$

* * * * *